United States Patent [19]
Ames, Jr. et al.

[11] Patent Number: 6,133,420
[45] Date of Patent: *Oct. 17, 2000

[54] GPR14 POLYPEPTIDES

[75] Inventors: Robert S. Ames, Jr., Havertown; Henry M. Sarau, Harleysville; James J. Foley, Radnor; Usman Shabon, Swarthmore; Derk Bergsma, Berwyn, all of Pa.; Jonathan K. Chambers, Haslingfield, United Kingdom

[73] Assignees: SmithKline Beecham Corporation, Philadelphia, Pa.; SmithKline Beecham plc, United Kingdom

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/058,725

[22] Filed: Apr. 10, 1998

Related U.S. Application Data

[63] Continuation-in-part of application No. 08/789,354, Jan. 27, 1997, Pat. No. 5,851,798
[60] Provisional application No. 60/074,075, Feb. 9, 1998.
[51] Int. Cl.$^7$ .................................................. C07K 14/705
[52] U.S. Cl. ........................ 530/350; 435/69.1; 530/300; 530/324; 530/326
[58] Field of Search ..................................... 530/350, 300, 530/326, 324; 435/69.1

[56] References Cited

U.S. PATENT DOCUMENTS 5,759,789  6/1998  Abramowitz et al. ................. 435/7.21

FOREIGN PATENT DOCUMENTS

0859052A1  8/1998  European Pat. Off. .
WO 9428931  12/1994  WIPO .

OTHER PUBLICATIONS

Mikayama et al. Molecukar cloning and functonal expression of a cDNA encoding glycosylation–inhibiting factor. Proc. Natl. Acad. Sci. 1993 vol. 90:10056–10060.

Voet et al. Biochemistry. 1990. John Wiley & Sons, Inc., pp. 126–128 and 228–234.

George et al., Macromolecular Sequencing and Synthesis, Selected Methods and Applications, 127–149, 1988, Alan R. Liss, Inc.

Yamada, Y. et al., "Somatostatin receptors, an expanding gene family:cloning and functional characterization of human SSTR3, a protein to adenylyl cyclase", *Molecular Endocrinology*, 6(12):2136–2142, 1992.

Tal, M. et al., "A novel putative neuropeptide receptor expressed in neural tissue, including sensory epithelia", *Biochem. and Biophys. Res. Commun.*, 209(2):752–759, 1995.

Marclese et al., "Cloning and Chromosomal Mapping of Three Novel Genes, GPR9, GPR10, and GPR14, Encoding Receptors Related to Interleukin 8, Neuropeptide Y and Somatostatin Receptors", *Genomics*, 29, 335–344, 1995.

Sambrook et al., "Molecular Cloning", *Cold Spring Harbor Laboratories*, 3, 16.2–16.30, 1989.

Sambrook et al., "Molecular Cloning", *Cold Spring Harbor Laboratories*, 3, 17.2–17.28, 1989.

Stadel et al. "Orphan G protein–coupled receptors: a neglected opportunity for pioneer drug discovery", Trends in Pharmacological Sciences, vol. 18, pp. 430–437 (1997).

Lee et al. "Molecular Biology of G–Protein–Coupled Receptors", Trends in Biomedical Research, vol. 6, pp. 488–497 (1993).

*Primary Examiner*—Christina Y. Chan
*Assistant Examiner*—Joseph F. Murphy
*Attorney, Agent, or Firm*—William T. Han; Ratner & Prestia; William T. King

[57] ABSTRACT

Human GPR14 polypeptides and polynucleotides and methods for producing such polypeptides by recombinant techniques are disclosed. Also disclosed are methods for utilizing Human GPR14 polypeptides and polynucleotides in the design of protocols for the treatment of infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others and diagnostic assays for such conditions.

7 Claims, 7 Drawing Sheets

Nucleotide and Amino Acid sequence of Human GPR14 (SEQ ID NOS: 1 and 2, respectively.)

```
            10                      30                      50
        GACAAAACTGGGTACGGGCCCCCCTCGAGGTCGACGGTATCGATAAGCTTGATATCGAAT
            70                      90                     110
        TCGTTTCCCTGTATGAGAAATGGAGATTGCAGAGGCCTTCCTCTCCTTACATGTTCTTCT
           130                     150                     170
        ATTTGGACTTTTAAAGTCAGTAGCTACTAGTTTTGCAATCTAAAGAAAACATTTTTTTAA
           190                     210                     230
        ATGTACAAGTCAAATAAATACGAgAAAGGACTCAGGAGTAAGTGGGCCCCACCTGTGCAC
           250                     270                     290
        AGACAAgAAAGTGAGGCCTGGGGGGGCGCACTGGGCAgAgCCCAGGACTCCCAGTTCTGT
           310                     330                     350
        CCACTGCCGACCTCTGCCCCAGGGGCTGCCCTCCTGTGTTCCGGCTTTCAgAAAAGCCCA
           370                     390                     410
        GTTCATCCCAgAgGCCATGGGACCTACAgTGAgGGGGGGGCAgGGGTCCTGCTGGGGCAT
           430                     450                     470
        GCGGGGGTCgGGGAgGGGGGTTGGGGCAgCTCGTCTGGTGGCTCTTGAGTCCTCCTGCAG
           490                     510                     530
        AgCTGGTGGCTTCCAgAgAGTCCCGAgAGTTGGAGGGCACTGGGGAgCCCACGTGACTCT
           550                     570                     590
        GTGGGAACgAgGCCATCACAGTGGCCTCCTGGGAgCGGAAgGTGTTGCCTGATTTGCTTC
           610                     630                     650
        TTTCCCCACAGGCTGAgCTGGTTGCCCACAGGGGCCCCCGCCCCATCTCAgGGAgTGTCC
           670                     690                     710
        ACCCAgCCCTGAgCCCGTCgTGAGGGGTCAgAgATGGCGCTGACCCCCgAGTCCCCGAGC
                                                 M  A  L  T  P  E  S  P  S
           730                     750                     770
        AGCTTCCCTGGGCTGGCCGCCACCGGCAGCTCTGTGCCGGAGCCGCCTGGCGGCCCCAAC
         S  F  P  G  L  A  A  T  G  S  S  V  P  E  P  P  G  G  P  N
           790                     810                     830
        GCAACCCTCAACAGCTCCTGGGCCAGCCCGACCGAGCCCAGCTCCCTGGAgGACCTGGTG
         A  T  L  N  S  S  W  A  S  P  T  E  P  S  S  L  E  D  L  V
           850                     870                     890
```

FIG. 1A

```
GCCACGGGCACCATTGGGACTCTGCTGTCGGCCATGGGCGTGGTGGGCGTGGTGGGCAAC
 A   T   G   T   I   G   T   L   L   S   A   M   G   V   V   G   V   V   G   N
        910                 930                 950
GCCTACACGCTGGTGGTCACCTGCCGCTCCCTGCGTGCGGTGGCCTCCATGTACGTCTAC
 A   Y   T   L   V   V   T   C   R   S   L   R   A   V   A   S   M   Y   V   Y
        970                 990                1010
GTGGTCAACCTGGCGCTGGCCGACCTGCTGTACCTGCTCAGCATCCCCTTCATCGTGGCC
 V   V   N   L   A   L   A   D   L   L   Y   L   L   S   I   P   F   I   V   A
       1030                1050                1070
ACCTACGTCACCAAGGAGTGGCACTTCGGGGAcGTGGGCTGCCGCGTGCTCTTCGGCCTG
 T   Y   V   T   K   E   W   H   F   G   D   V   G   C   R   V   L   F   G   L
       1090                1110                1130
GACTTCCTGACCATGCACGCCAGCATCTTCACGCTGACCGTCATGAgCAGCGAgCGCTAC
 D   F   L   T   M   H   A   S   I   F   T   L   T   V   M   S   S   E   R   Y
       1150                1170                1190
GCTGCGGTGCTGCGGCCGCTGGACACCGTGCAGCGCCCCAAGGGCTACCGCAAGCTGCTG
 A   A   V   L   R   P   L   D   T   V   Q   R   P   K   G   Y   R   K   L   L
       1210                1230                1250
GCGCTGGGCACCTGGCTGCTGGCGCTGCTGCTGACgCTGCCCGTGATGCTGGCCATGCGG
 A   L   G   T   W   L   L   A   L   L   L   T   L   P   V   M   L   A   M   R
       1270                1290                1310
CTGGTGCGCCGGGGTCcCAAgAgCCTGTGCCTGCCCGCCTGGGGCCCGCGCGCCCACCGC
 L   V   R   R   G   P   K   S   L   C   L   P   A   W   G   P   R   A   H   R
       1330                1350                1370
GCCTACCTGACGCTGCTCTTCGCCACCAGCATCGCGGGGCCCGGGCTGCTCATCGGGCTG
 A   Y   L   T   L   L   F   A   T   S   I   A   G   P   G   L   L   I   G   L
       1390                1410                1430
CTCTACGCGCGCCTGGCCCGCGCCTACCGCCGCTCGCAGCGCGCCTCCTTCAAGCGGGCC
 L   Y   A   R   L   A   R   A   Y   R   R   S   Q   R   A   S   F   K   R   A
       1450                1470                1490
CGGCGGCCGGGGGCGCGCGCGCTGCGCCTGGTGCTGGGCATCGTGCTGCTCTTCTGGGCC
 R   R   P   G   A   R   A   L   R   L   V   L   G   I   V   L   L   F   W   A
       1510                1530                1550
TGCTTCCTGCCCTTCTGGCTGTGGCAGCTGCTCGCCCAGTACCACCAGGCCCCGCTGGCG
 C   F   L   P   F   W   L   W   Q   L   L   A   Q   Y   H   Q   A   P   L   A
       1570                1590                1610
```

FIG. 1B

```
CCGCGGACGGCGCGCATCGTCAACTACCTGACCACCTGCCTCACCTACGGCAACAGCTGC
 P   R   T   A   R   I   V   N   Y   L   T   T   C   L   T   Y   G   N   S   C
         1630                1650                1670
GCCAACCCCTTCCTCTACACGCTGCTCACCAGGAACTACCGCGACCACCTGCGCGGCCGC
 A   N   P   F   L   Y   T   L   L   T   R   N   Y   R   D   H   L   R   G   R
         1690                1710                1730
GTGCGGGGCCCGGGCAGCGGGGGAGGCCGGGGGCCCGTTCCCTCCCTGCAGCCCCGCGCC
 V   R   G   P   G   S   G   G   G   R   G   P   V   P   S   L   Q   P   R   A
         1750                1770                1790
CGCTTCCAGCGCTGTTCGGGCCGCTCCCTGTCTTCCTGCAGCCCACAGCCCACTGACAGC
 R   F   Q   R   C   S   G   R   S   L   S   S   C   S   P   Q   P   T   D   S
         1810                1830                1850
CTCGTGCTGGCCCCAGCGGCCCCGGCCCGACCTGCGCCCGAgGGTCCCAGGGCCCCGGCG
 L   V   L   A   P   A   A   P   A   R   P   A   P   E   G   P   R   A   P   A
         1870                1890                1910
TGAGCACGCGGAGGGGCGGCTGGAGTCCAgGCGGGGACgCGCCCCAAAGCCCCAGCCACT
 *
         1930                1950                1970
CCCGGGAGCCCCCCCAACTCCCAAATCACAGGCCCTGCCCCTCCTCCGTCCCCTTCTGGA
         1990                2010                2030
AAGATcCTGCTCGCTTCCCCTCAgCGCCCTTCCCGTGATGCCCAgAAgCGCCCAcCCGCC
         2050                2070                2090
TCCCTGAgGGTcTCCAgGAgGcTCCAgCGCAgTCCCGGCTTCTGGAgAcATGGcTTCgTC
         2110
ACAgAgGGcAgCAGGcGCCATTGCCC
```

FIG. 1C

Amino acid sequence of Rat GPR14

```
  1  MALSLESTTS FHMLTVSGST VTELPGDSNV SLNSSWSGPT DPSSLKDLVA
 51  TGVIGAVLSA MGVVGMVGNV YTLVVMCRFL RASASMYVYV VNLALADLLY
101  LLSIPFIIAT YVTKDWHFGD VGCRVLFSLD FLTMHASIFT LTIMSSERYA
151  AVLRPLDTVQ RSKGYRKLLV LGTWLLALLL TLPMMLAIQL VRRGSKSLCL
201  PAWGPRAHRT YLTLLFGTSI VGPGLVIGLL YVRLARAYWL SQQASFKQTR
251  RLPNPRVLYL ILGIVLLFWA CFLPFWLWQL LAQYHEAMPL TPETARIVNY
301  LTTCLTYGNS CINPLLYTLL TKNYREYLRG RQRSLGSSCH SPGSPGSFLP
351  SRVHLQQDSG RSLSSSSQQA TETLMLSPVP RNGALL
```

Nucleotide sequence of rat GPR14

```
  1  GGGACAGTGG GTCCCAATGG CTCTAGGGTC CTCCTGTGTA GCTGGGGAGA
 51  TAACAAAAAA GGGATTCTTT TGAGGCTTCC AACAGGATAT AGGACCTGGT
101  GAGCCTTTGT CTCTCTGCAT AGGGACAGTG ACTGTGTCCA TCACAGAGGC
151  TGTTTAGGGC ATAGAAGTAG GTTACTGCCT TGAACCTCTG ACACTAATCT
201  TTTCCCACAG GACAAGTTTC CCACGGGCTC TCCTCACTGA GCAGTGGTTC
251  TCCCCCTGGA ATCCCAGTGT GAGGACCGAG ATGGCTCTGA GCCTGGAGTC
301  TACAACAAGC TTTCATATGC TCACCGTGTC CGGAAGCACT GTGACTGAGC
351  TGCCTGGTGA CTCCAACGTG TCCCTCAACA GTTCCTGGTC CGGCCCAACA
401  GATCCCAGCT CCCTGAAAGA CCTTGTGGCC ACGGGTGTCA TCGGGGCAGT
451  GCTCTCAGCC ATGGGTGTGG TGGGCATGGT GGGAAATGTA TACACTTTGG
501  TGGTCATGTG CCGGTTTCTG CGTGCCTCGG CCTCCATGTA CGTCTATGTG
551  GTCAACCTAG CGCTGGCTGA TCTGCTGTAC CTGCTGAGCA TTCCCTTCAT
601  CATAGCCACC TACGTCACTA AGGACTGGCA CTTTGGAGAT GTGGGCTGCA
651  GAGTCCTCTT TAGCCTGGAC TTCCTGACAA TGCACGCCAG CATCTTCACC
701  CTGACCATAA TGAGCAGCGA ACGCTATGCA GCCGTACTGA GGCCTCTGGA
751  CACAGTCCAG CGCTCCAAGG GTTACCGTAA GCTGCTGGTG CTGGGCACCT
801  GGTTGCTGGC ACTGCTGCTG ACCCTACCCA TGATGCTTGC CATCCAGCTG
851  GTCCGCAGGG GCTCTAAGAG CCTCTGCCTG CCAGCCTGGG GCCCTCGTGC
```

FIG. 2A

```
 901  CCACCGTACT TACCTAACGT TGCTCTTTGG GACCAGCATT GTGGGGCCTG
 951  GCTTGGTCAT TGGGCTGCTC TATGTCCGTC TGGCCAGGGC CTACTGGCTA
1001  TCTCAGCAAG CTTCTTTCAA GCAGACACGG CGGCTGCCCA ACCCCAGGGT
1051  GCTCTACCTC ATCCTTGGTA TCGTCCTTCT CTTCTGGGCC TGCTTTCTAC
1101  CCTTCTGGCT GTGGCAGCTG CTGGCCCAGT ACCACGAGGC CATGCCACTG
1151  ACTCCCGAGA CTGCACGCAT TGTCAACTAC CTGACCACCT GCCTCACTTA
1201  TGGCAACAGT TGCATCAATC CCTTGCTCTA CACTCTGCTC ACCAAGAACT
1251  ATCGAGAGTA CCTACGTGGC CGCCAGCGGT CACTGGGTAG TAGTTGCCAC
1301  AGCCCAGGGA GTCCTGGCAG CTTCCTGCCC AGCCGAGTCC ACCTCCAGCA
1351  GGACTCGGGC CGCTCGCTGT CCTCCAGCAG CCAACAGGCC ACAGAGACCC
1401  TCATGCTGTC TCCAGTCCCC CGTAACGGGG CCCTTCTCTG AGAGTGCACT
1451  GTGCAATCCT GGCATAGGAA AGGACCCAAA GGCGTGCGGC TCCGGAGCGC
1501  ATTTCCCAGA ATCCCCTGCT CAAACCTAAC TGGCTCGTC
```

FIG. 2B

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2126 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GACAAAACTG GGTACGGGCC CCCCTCGAGG TCGACGGTAT CGATAAGCTT GATATCGAAT      60

TCGTTTCCCT GTATGAGAAA TGGAGATTGC AGAGGCCTTC CTCTCCTTAC ATGTTCTTCT     120

ATTTGGACTT TTAAAGTCAG TAGCTACTAG TTTTGCAATC TAAAGAAAAC ATTTTTTTAA     180

ATGTACAAGT CAAATAAATA CGAGAAAGGA CTCAGGAGTA AGTGGGCCCC ACCTGTGCAC     240

AGACAAGAAA GTGAGGCCTG GGGGGCGCA  CTGGGCAGAG CCCAGGACTC CCAGTTCTGT     300

CCACTGCCGA CCTCTGCCCC AGGGGCTGCC CTCCTGTGTT CCGGCTTTCA GAAAAGCCCA     360

GTTCATCCCA GAGGCCATGG GACCTACAGT GAGGGGGGG  CAGGGGTCCT GCTGGGGCAT     420

GCGGGGGTCG GGGAGGGGG  TTGGGCAGC  TCGTCTGGTG GCTCTTGAGT CCTCCTGCAG     480

AGCTGGTGGC TTCCAGAGAG TCCCGAGAGT TGGAGGGCAC TGGGGAGCCC ACGTGACTCT     540

GTGGGAACGA GGCCATCACA GTGGCCTCCT GGGAGCGGAA GGTGTTGCCT GATTTGCTTC     600
```

```
TTTCCCCACA GGCTGAGCTG GTTGCCCACA GGGGCCCCCG CCCCATCTCA GGGAGTGTCC      660

ACCCAGCCCT GAGCCCGTCG TGAGGGGTCA GAGATGGCGC TGACCCCCGA GTCCCCGAGC      720

AGCTTCCCTG GGCTGGCCGC CACCGGCAGC TCTGTGCCGA AGCCGCCTGG CGGCCCCAAC      780

GCAACCCTCA ACAGCTCCTG GGCCAGCCCG ACCGAGCCCA GCTCCCTGGA GGACCTGGTG      840

GCCACGGGCA CCATTGGGAC TCTGCTGTCG GCCATGGGCG TGGTGGGCGT GGTGGGCAAC      900

GCCTACACGC TGGTGGTCAC CTGCCGCTCC CTGCGTGCGG TGGCCTCCAT GTACGTCTAC      960

GTGGTCAACC TGGCGCTGGC CGACCTGCTG TACCTGCTCA GCATCCCCTT CATCGTGGCC     1020

ACCTACGTCA CCAAGGAGTG GCACTTCGGG ACGTGGGCT GCCGCGTGCT CTTCGGCCTG     1080

GACTTCCTGA CCATGCACGC CAGCATCTTC ACGCTGACCG TCATGAGCAG CGAGCGCTAC     1140

GCTGCGGTGC TGCGGCCGCT GGACACCGTG CAGCGCCCCA AGGGCTACCG CAAGCTGCTG     1200

GCGCTGGGCA CCTGGCTGCT GGCGCTGCTG CTGACGCTGC CCGTGATGCT GGCCATGCGG     1260

CTGGTGCGCC GGGGTCCCAA GAGCCTGTGC CTGCCCGCCT GGGGCCCGCG CGCCCACCGC     1320

GCCTACCTGA CGCTGCTCTT CGCCACCAGC ATCGCGGGGC CCGGGCTGCT CATCGGGCTG     1380

CTCTACGCGC GCCTGGCCCG CGCCTACCGC CGCTCGCAGC GCGCCTCCTT CAAGCGGGCC     1440

CGGCGGCCGG GGGCGCGCGC GCTGCGCCTG GTGCTGGGCA TCGTGCTGCT CTTCTGGGCC     1500

TGCTTCCTGC CCTTCTGGCT GTGGCAGCTG CTCGCCCAGT ACCACCAGGC CCCGCTGGCG     1560

CCGCGGACGG CGCGCATCGT CAACTACCTG ACCACCTGCC TCACCTACGG CAACAGCTGC     1620

GCCAACCCCT TCCTCTACAC GCTGCTCACC AGGAACTACC GCGACCACCT GCGCGGCCGC     1680

GTGCGGGGCC CGGGCAGCGG GGGAGGCCGG GGGCCCGTTC CCTCCCTGCA GCCCCGCGCC     1740

CGCTTCCAGC GCTGTTCGGG CCGCTCCCTG TCTTCCTGCA GCCCACAGCC CACTGACAGC     1800

CTCGTGCTGG CCCCAGCGGC CCCGGCCCGA CCTGCGCCCG AGGGTCCCAG GGCCCCGGCG     1860

TGAGCACGCG GAGGGGCGGC TGGAGTCCAG GCGGGGACGC GCCCCAAAGC CCCAGCCACT     1920

CCCGGGAGCC CCCCCAACTC CCAAATCACA GGCCCTGCCC CTCCTCCGTC CCCTTCTGGA     1980

AAGATCCTGC TCGCTTCCCC TCAGCGCCCT TCCCGTGATG CCCAGAAGCG CCCACCCGCC     2040

TCCCTGAGGG TCTCCAGGAG GCTCCAGCGC AGTCCCGGCT TCTGGAGACA TGGCTTCGTC     2100

ACAGAGGGCA GCAGGCGCCA TTGCCC                                         2126
```

(2) INFORMATION FOR SEQ ID NO:2:

(i) SEQUENCE CHARACTERISTICS:
        (A) LENGTH: 389 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ala Leu Thr Pro Glu Ser Pro Ser Ser Phe Pro Gly Leu Ala Ala
  1               5                  10                  15

Thr Gly Ser Ser Val Pro Glu Pro Pro Gly Gly Pro Asn Ala Thr Leu
             20                  25                  30

Asn Ser Ser Trp Ala Ser Pro Thr Glu Pro Ser Ser Leu Glu Asp Leu
         35                  40                  45

Val Ala Thr Gly Thr Ile Gly Thr Leu Leu Ser Ala Met Gly Val Val
     50                  55                  60

Gly Val Val Gly Asn Ala Tyr Thr Leu Val Val Thr Cys Arg Ser Leu
```

```
                65                  70                  75                  80
Arg Ala Val Ala Ser Met Tyr Val Tyr Val Val Asn Leu Ala Leu Ala
                            85                  90                  95

Asp Leu Leu Tyr Leu Leu Ser Ile Pro Phe Ile Val Ala Thr Tyr Val
            100                 105                 110

Thr Lys Glu Trp His Phe Gly Asp Val Gly Cys Arg Val Leu Phe Gly
        115                 120                 125

Leu Asp Phe Leu Thr Met His Ala Ser Ile Phe Thr Leu Thr Val Met
    130                 135                 140

Ser Ser Glu Arg Tyr Ala Ala Val Leu Arg Pro Leu Asp Thr Val Gln
145                 150                 155                 160

Arg Pro Lys Gly Tyr Arg Lys Leu Leu Ala Leu Gly Thr Trp Leu Leu
                165                 170                 175

Ala Leu Leu Leu Thr Leu Pro Val Met Leu Ala Met Arg Leu Val Arg
            180                 185                 190

Arg Gly Pro Lys Ser Leu Cys Leu Pro Ala Trp Gly Pro Arg Ala His
        195                 200                 205

Arg Ala Tyr Leu Thr Leu Leu Phe Ala Thr Ser Ile Ala Gly Pro Gly
    210                 215                 220

Leu Leu Ile Gly Leu Leu Tyr Ala Arg Leu Ala Arg Ala Tyr Arg Arg
225                 230                 235                 240

Ser Gln Arg Ala Ser Phe Lys Arg Ala Arg Pro Gly Ala Arg Ala
                245                 250                 255

Leu Arg Leu Val Leu Gly Ile Val Leu Leu Phe Trp Ala Cys Phe Leu
            260                 265                 270

Pro Phe Trp Leu Trp Gln Leu Leu Ala Gln Tyr His Gln Ala Pro Leu
        275                 280                 285

Ala Pro Arg Thr Ala Arg Ile Val Asn Tyr Leu Thr Thr Cys Leu Thr
    290                 295                 300

Tyr Gly Asn Ser Cys Ala Asn Pro Phe Leu Tyr Thr Leu Leu Thr Arg
305                 310                 315                 320

Asn Tyr Arg Asp His Leu Arg Gly Arg Val Arg Gly Pro Gly Ser Gly
                325                 330                 335

Gly Gly Arg Gly Pro Val Pro Ser Leu Gln Pro Arg Ala Arg Phe Gln
            340                 345                 350

Arg Cys Ser Gly Arg Ser Leu Ser Ser Cys Ser Pro Gln Pro Thr Asp
        355                 360                 365

Ser Leu Val Leu Ala Pro Ala Pro Ala Arg Pro Ala Pro Glu Gly
    370                 375                 380

Pro Arg Ala Pro Ala
385

(2) INFORMATION FOR SEQ ID NO:3:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Ala Gly Thr Ala Asp Cys Phe Trp Lys Tyr Cys Val
1               5                   10
```

(2) INFORMATION FOR SEQ ID NO:4:

(i) SEQUENCE CHARACTERISTICS:
        (A) LENGTH: 386 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ala Leu Ser Leu Glu Ser Thr Thr Ser Phe His Met Leu Thr Val
 1               5                  10                  15

Ser Gly Ser Thr Val Thr Glu Leu Pro Gly Asp Ser Asn Val Ser Leu
                20                  25                  30

Asn Ser Ser Trp Ser Gly Pro Thr Asp Pro Ser Ser Leu Lys Asp Leu
            35                  40                  45

Val Ala Thr Gly Val Ile Gly Ala Val Leu Ser Ala Met Gly Val Val
        50                  55                  60

Gly Met Val Gly Asn Val Tyr Thr Leu Val Val Met Cys Arg Phe Leu
65                  70                  75                  80

Arg Ala Ser Ala Ser Met Tyr Val Tyr Val Val Asn Leu Ala Leu Ala
                85                  90                  95

Asp Leu Leu Tyr Leu Leu Ser Ile Pro Phe Ile Ile Ala Thr Tyr Val
               100                 105                 110

Thr Lys Asp Trp His Phe Gly Asp Val Gly Cys Arg Val Leu Phe Ser
           115                 120                 125

Leu Asp Phe Leu Thr Met His Ala Ser Ile Phe Thr Leu Thr Ile Met
130                 135                 140

Ser Ser Glu Arg Tyr Ala Ala Val Leu Arg Pro Leu Asp Thr Val Gln
145                 150                 155                 160

Arg Ser Lys Gly Tyr Arg Lys Leu Leu Val Leu Gly Thr Trp Leu Leu
                165                 170                 175

Ala Leu Leu Leu Thr Leu Pro Met Met Leu Ala Ile Gln Leu Val Arg
            180                 185                 190

Arg Gly Ser Lys Ser Leu Cys Leu Pro Ala Trp Gly Pro Arg Ala His
        195                 200                 205

Arg Thr Tyr Leu Thr Leu Leu Phe Gly Thr Ser Ile Val Gly Pro Gly
    210                 215                 220

Leu Val Ile Gly Leu Leu Tyr Val Arg Leu Ala Arg Ala Tyr Trp Leu
225                 230                 235                 240

Ser Gln Gln Ala Ser Phe Lys Gln Thr Arg Arg Leu Pro Asn Pro Arg
                245                 250                 255

Val Leu Tyr Leu Ile Leu Gly Ile Val Leu Leu Phe Trp Ala Cys Phe
            260                 265                 270

Leu Pro Phe Trp Leu Trp Gln Leu Leu Ala Gln Tyr His Glu Ala Met
        275                 280                 285

Pro Leu Thr Pro Glu Thr Ala Arg Ile Val Asn Tyr Leu Thr Thr Cys
    290                 295                 300

Leu Thr Tyr Gly Asn Ser Cys Ile Asn Pro Leu Leu Tyr Thr Leu Leu
305                 310                 315                 320

Thr Lys Asn Tyr Arg Glu Tyr Leu Arg Gly Arg Gln Arg Ser Leu Gly
                325                 330                 335

Ser Ser Cys His Ser Pro Gly Ser Pro Gly Ser Phe Leu Pro Ser Arg
            340                 345                 350

Val His Leu Gln Gln Asp Ser Gly Arg Ser Leu Ser Ser Ser Ser Gln
```

```
              355                 360                 365
Gln Ala Thr Glu Thr Leu Met Leu Ser Pro Val Pro Arg Asn Gly Ala
        370                 375                 380
Leu Leu
385

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Glu Thr Pro Asp Cys Phe Trp Lys Tyr Cys Val
 1               5                  10

(2) INFORMATION FOR SEQ ID NO:6:

(i) SEQUENCE CHARACTERISTICS:
        (A) LENGTH: 1539 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GGGACAGTGG GTCCCAATGG CTCTAGGGTC CTCCTGTGTA GCTGGGGAGA TAACAAAAAA      60

GGGATTCTTT TGAGGCTTCC AACAGGATAT AGGACCTGGT GAGCCTTTGT CTCTCTGCAT     120

AGGGACAGTG ACTGTGTCCA TCACAGAGGC TGTTTAGGGC ATAGAAGTAG GTTACTGCCT     180

TGAACCTCTG ACACTAATCT TTTCCCACAG GACAAGTTTC CCACGGGCTC TCCTCACTGA     240

GCAGTGGTTC TCCCCCTGGA ATCCCAGTGT GAGGACCGAG ATGGCTCTGA GCCTGGAGTC     300

TACAACAAGC TTTCATATGC TCACCGTGTC CGGAAGCACT GTGACTGAGC TGCCTGGTGA     360

CTCCAACGTG TCCCTCAACA GTTCCTGGTC CGGCCCAACA GATCCCAGCT CCCTGAAAGA     420

CCTTGTGGCC ACGGGTGTCA TCGGGGCAGT GCTCTCAGCC ATGGGTGTGG TGGGCATGGT     480

GGGAAATGTA TACACTTTGG TGGTCATGTG CCGGTTTCTG CGTGCCTCGG CCTCCATGTA     540

CGTCTATGTG GTCAACCTAG CGCTGGCTGA TCTGCTGTAC CTGCTGAGCA TTCCCTTCAT     600

CATAGCCACC TACGTCACTA AGGACTGGCA CTTTGGAGAT GTGGGCTGCA GAGTCCTCTT     660

TAGCCTGGAC TTCCTGACAA TGCACGCCAG CATCTTCACC CTGACCATAA TGAGCAGCGA     720

ACGCTATGCA GCCGTACTGA GGCCTCTGGA CACAGTCCAG CGCTCCAAGG GTTACCGTAA     780

GCTGCTGGTG CTGGGCACCT GGTTGCTGGC ACTGCTGCTG ACCCTACCCA TGATGCTTGC     840

CATCCAGCTG GTCCGCAGGG GCTCTAAGAG CCTCTGCCTG CCAGCCTGGG GCCCTCGTGC     900

CCACCGTACT TACCTAACGT TGCTCTTTGG ACCAGCATT GTGGGGCCTG GCTTGGTCAT     960

TGGGCTGCTC TATGTCCGTC TGGCCAGGGC CTACTGGCTA TCTCAGCAAG CTTCTTTCAA    1020

GCAGACACGG CGGCTGCCCA ACCCCAGGGT GCTCTACCTC ATCCTTGGTA TCGTCCTTCT    1080

CTTCTGGGCC TGCTTTCTAC CCTTCTGGCT GTGGCAGCTG CTGGCCCAGT ACCACGAGGC    1140

CATGCCACTG ACTCCCGAGA CTGCACGCAT TGTCAACTAC CTGACCACCT GCCTCACTTA    1200

TGGCAACAGT TGCATCAATC CCTTGCTCTA CACTCTGCTC ACCAAGAACT ATCGAGAGTA    1260
```

| | | | | |
|---|---|---|---|---|
| CCTACGTGGC | CGCCAGCGGT | CACTGGGTAG | TAGTTGCCAC | AGCCCAGGGA | GTCCTGGCAG | 1320 |
| CTTCCTGCCC | AGCCGAGTCC | ACCTCCAGCA | GGACTCGGGC | CGCTCGCTGT | CCTCCAGCAG | 1380 |
| CCAACAGGCC | ACAGAGACCC | TCATGCTGTC | TCCAGTCCCC | CGTAACGGGG | CCCTTCTCTG | 1440 |
| AGAGTGCACT | GTGCAATCCT | GGCATAGGAA | AGGACCCAAA | GGCGTGCGGC | TCCGGAGCGC | 1500 |
| ATTTCCCAGA | ATCCCCTGCT | CAAACCTAAC | TGGCTCGTC | | | 1539 |

GPR14 POLYPEPTIDES

This application claims priority from U.S. Provisional Application Ser. No. 60/074,075 filed Feb. 9, 1998. This application is also a Continuation-in-Part of U.S. Ser. No. 08/789,354 filed Jan. 27, 1997, now U.S. Pat. No. 5,851,798.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to G-Protein coupled receptor, hereinafter referred to as Human GPR14. The invention also relates to inhibiting or activating the action of such polynucleotides and polypeptides.

BACKGROUND OF THE INVENTION

It is well established that many medically significant biological processes are mediated by proteins participating in signal transduction pathways that involve G-proteins and/or second messengers, e.g., cAMP (Lefkowitz, Nature, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K., et al., Proc. Natl Acad. Sci., USA, 1987, 84:46–50; Kobilka, B. K., et al., Science, 1987, 238:650–656; Bunzow, J. R., et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect of hormone binding is activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane a-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Most G-protein coupled receptors (or otherwise known as 7TM receptors) have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said socket being surrounded by hydrophobic residues of the G-protein coupled receptors. The hydrophilic side of each G-protein coupled receptor transmembrane helix is postulated to face inward and form polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc. Rev., 1989, 10:317–331) Different G-protein a-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 transmembrane (7 TM) receptors have been successfully introduced onto the market.

This indicates that these receptors have an established, proven history as therapeutic targets. Clearly there is a need for identification and characterization of further receptors which can play a role in preventing, ameliorating or correcting dysfunctions or diseases, including, but not limited to, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

SUMMARY OF THE INVENTION

In one aspect, the invention relates to Human GPR14 polypeptides and recombinant materials and methods for their production. Another aspect of the invention relates to methods for using such Human GPR14 polypeptides and polynucleotides. Such uses include the treatment of infections such as bacterial, fungal, protozoan and viral infections, particularly infections caused by HIV-1 or HIV- 2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

In accordance with another aspect of the present invention there are provided methods of screening for compounds which bind to and activate (agonist) or inhibit activation (antagonist) of rat or Human GPR 14 polypeptides (receptors), and for their ligands.

In particular, the preferred method for identifying agonist or antagonist of a Human or rat GPR 14 polypeptide comprises:

contacting a cell expressing on the surface thereof the polypeptide, said polypeptide being associated with a second component capable of providing a detectable signal in response to the binding of a compound to said polypeptide, with a compound to be screened under conditions to permit binding to the polypeptide; and determining whether the compound binds to and activates or inhibits the polypeptide by measuring the level of a signal generated from the interaction of the compound with the polypeptide.

In a further preferred embodiment, the method further comprises conducting the identification of agonist or antagonist in the presence of labeled or unlabeled, fish or Human urotensin II.

In another embodiment of the method for identifying agonist or antagonist of a human or rat GPR 14 polypeptide comprises:

determining the inhibition of binding of a ligand to cells which have the polypeptide on the surface thereof, or to cell membranes containing the polypeptide, in the presence of a candidate compound under conditions to permit binding to the polypeptide, and determining the amount of ligand bound to the polypeptide, such that a compound capable of causing reduction of binding of a ligand is an agonist or antagonist. Preferably the ligand is human or rat urotensin II. Yet more preferably human or rat urotensin II is labeled.

Further the present invention relates to treating conditions associated with Human GPR14 imbalance with the identified compounds. Yet another aspect of the invention relates to diagnostic assays for detecting diseases associated with inappropriate Human GPR14 activity or levels.

BRIEF DESCRIPTION OF THE DRAWINGS

FIGS. 1A–1C show the nucleotide and deduced amino acid sequence of Human GPR14. SEQ ID NOS: 1 and 2.

FIGS. 2A–2B show the amino acid sequence and polynucleotide sequence of rat GPR14 receptor. SEQ ID NO: 4 and 6.

DESCRIPTION OF THE INVENTION

Definitions

Figure 3:
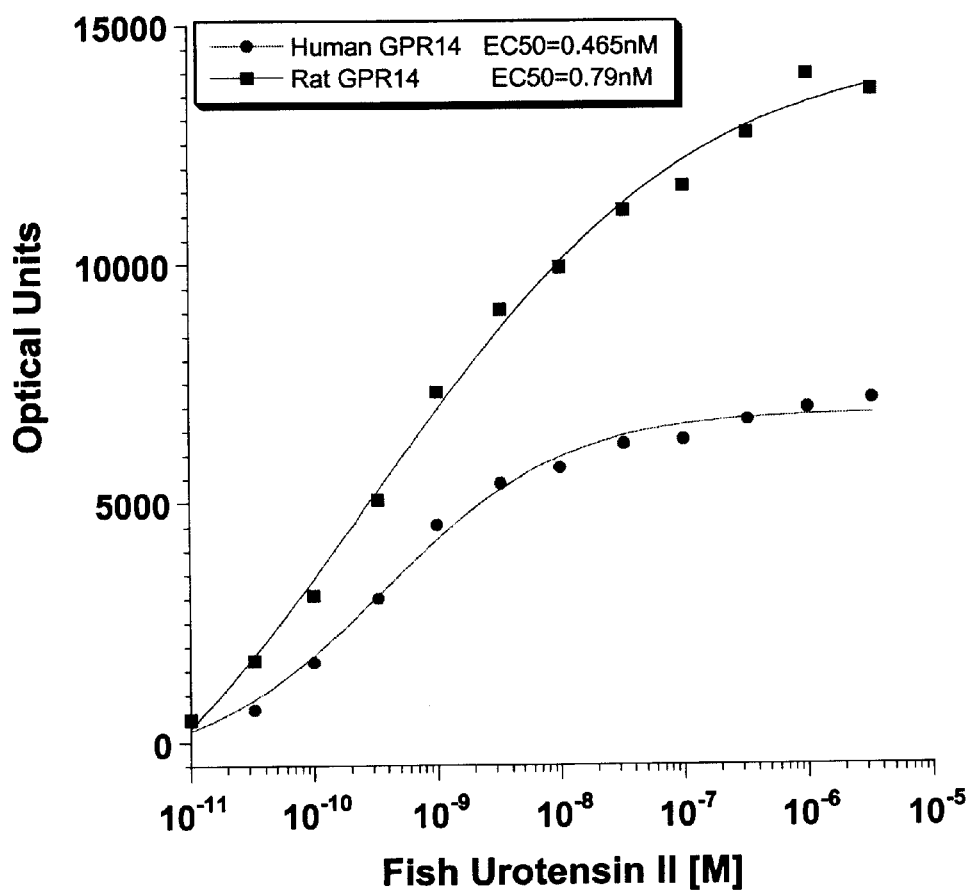
FIG. 3 shows concentration response curves for fish urotensin II against HEK 293 rat and Human GPR14 transients+G alpha-16 using FLIPR.

The following definitions are provided to facilitate understanding of certain terms used frequently herein.

"Human GPR14" refers generally to a polypeptide having the amino acid sequence set forth in SEQ ID NO:2, or an allelic variant thereof.

"Fish urotensin II" refers to polypeptide with amino acid sequence of Ala-Gly-Thr-Ala-Asp-Cys-Phe-Trp-Lys-Tyr-Cys-Val (SEQ ID NO:3), which is described by Pearson et al., in Proc Natl Acad Sci U S A 1980 August; 77(8) :5021–5024.

"Rat GPR14 receptor" or "rat GPR 14 receptor polypeptide" is a protein with GenBank Accession number U32673, and described by Marchese et al., in Genomics Sep. 20, 1995;29(2):335–344. Rat GPR14 receptor has amino acid sequence shown in FIGS. 2A–2B (SEQ ID NO: 4).

"Human urotensin II" is a protein with the amino acid sequence ETPDCFWKYCV (SEQ ID NO: 5). "Receptor Activity" or "Biological Activity of the Receptor" refers to the metabolic or physiologic function of said Human GPR14 including similar activities or improved activities or these activities with decreased undesirable side-effects. Also included are antigenic and immunogenic activities of said Human GPR14.

"Human GPR14 polypeptides" refers to polypeptides with amino acid sequences sufficiently similar to Human GPR14 sequences, preferably exhibiting at least one biological activity of the receptor.

"Human GPR14 gene" refers to a polynucleotide having the nucleotide sequence set forth in SEQ ID NO:1 or allelic variants thereof and/or their complements.

"Human GPR14 polynucleotides" refers to polynucleotides containing a nucleotide sequence which encodes a Human GPR14 polypeptide or fragment thereof, or a nucleotide sequence which has at least 75.9% identity to a nucleotide sequence encoding the polypeptide of SEQ ID NO:2 or the corresponding fragment thereof, or a nucleotide sequence which has sufficient identity to a nucleotide sequence contained in SEQ ID NO:1 to hybridize under conditions useable for amplification or for use as a probe or marker.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48. 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md 20894; Altschul, S., et al., *J. Mol. Biol.* 215: 403–410 (1990). The well known Smith Waterman algorithm may also be used to determine identity.

Preferred parameters for polypeptide sequence comparison include the following:

1) Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, J. Mol Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

Preferred polynucleotide embodiments further include an isolated polynucleotide comprising a polynucleotide sequence having at least a 50, 60, 70, 80, 85, 90, 95, 97 or 100% identity to the reference sequence of SEQ ID NO:1, wherein said polynucleotide sequence may be identical to the reference sequence of SEQ ID NO: 1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or: $n_n x_n - (x_n y)$, wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one nucleic acid deletion, substitution, , including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of amino acids in SEQ ID NO:2 by the integer defining the percent identity divided by 100 and then subtracting that product from said total number of amino acids in SEQ ID NO:2, or: $n_n = x_n - (x_n y)$, wherein $n_n$ is the number of amino acid alterations, $x_n$ is the total number of amino acids in SEQ ID NO:2, y is, for instance 0.70 for 70%, 0.80 for 80%, 0.85 for 85% etc., , is the symbol for the multiplication operator, and wherein any non-integer product of $x_n$ and y is rounded down to the nearest integer prior to subtracting it from $x_n$.

Preferred polypeptide embodiments further include an isolated polypeptide comprising a polypeptide having at least a 50,60, 70, 80, 85, 90, 95, 97 or 100% identity to a polypeptide reference sequence of SEQ ID NO:2, wherein said polypeptide sequence may be identical to the reference sequence of SEQ ID NO: 2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or: $n_a x_a - (x_a y)$, wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or: $n_a = x_a - (x_a y)$, wherein $n_a$ is the number of amino acid alterations, $x_a$ is the total number of amino acids in SEQ ID NO:2, y is, for instance 0.70 for 70%, 0.80 for 80%, 0.85 for 85% etc., and is the symbol for the multiplication operator, and wherein any non-integer product of $x_a$ and y is rounded down to the nearest integer prior to subtracting it from $x_a$.

Polypeptides of the Invention

The Human GPR14 polypeptides of the present invention include the polypeptide of SEQ ID NO:2 (in particular the mature polypeptide) as well as Human GPR14 polypeptides and which have at least 84.25% identity to the polypeptide of SEQ ID NO:2 or the relevant portion and more preferably at least 85% identity, and still more preferably at least 90% identity, and even still more preferably at least 95% identity to SEQ ID NO: 2.

The Human GPR14 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Biologically active fragments of the Human GPR14 polypeptides are also included in the invention. A fragment is a polypeptide having an amino acid sequence that entirely is the same as part, but not all, of the amino acid sequence of the aforementioned Human GPR14 polypeptides. As with Human GPR14 polypeptides, fragments may be "freestanding," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of Human GPR14 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of Human GPR14 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate receptor activity, including those with a similar activity or an improved activity, or with a decreased undesirable activity. Also included are those that are antigenic or immunogenic in an animal, especially in a human.

Thus, the polypeptides of the invention include polypeptides having an amino acid sequence at least 84.25% identical to that of SEQ ID NO:2 or fragments thereof with at least 84.25% identity to the corresponding fragment of SEQ ID NO:2. Preferably, all of these polypeptides retain the biological activity of the receptor, including antigenic activity. Included in this group are variants of the defined sequence and fragments. Preferred variants are those that vary from the referents by conservative amino acid substitutions—i.e., those that substitute a residue with another of like characteristics. Typical such substitutions are among Ala, Val, Leu and lie; among Ser and Thr; among the acidic residues Asp and Glu; among Asn and Gin; and among the basic residues Lys and Arg; or aromatic residues Phe and Tyr. Particularly preferred are variants in which several, 5–10, 1–5, or 1–2 amino acids are substituted, deleted, or added in any combination.

The Human GPR14 polypeptides of the invention can be prepared in any suitable manner. Such polypeptides include isolated naturally occurring polypeptides, recombinantly produced polypeptides, synthetically produced polypeptides, or polypeptides produced by a combination of these methods.

Means for preparing such polypeptides are well understood in the art.

Polynucleotides of the Invention

Another aspect of the invention relates to isolated polynucleotides which encode the Human GPR14 polypeptides and polynucleotides closely related thereto.

Human GPR 14 of the invention is structurally related to other proteins of the G-Protein coupled receptor, as shown by the results of sequencing the cDNA encoding Human GPR14. The cDNA sequence contains an open reading frame encoding a protein of 390 with a deduced molecular weight of kDa. Human GPR14 of FIGS. 1A–1C (SEQ ID NO:2) has about 84.25% identity (using Fasta) in 387 amino acid residues with *Rattus norvegicus* GPR14 orphan receptor (A. Marches, et al., Genomics 29(2):335–344, 1995). Furthermore, human GPR14 (SEQ. ID NO:2) is 31.7% identical to human Somatostatin-3 receptor over 331 amino acid residues (Y. Yamada et al., Mol. Endocrinol. 6(12) :2136–2142, 1992). Human GPR14 gene of FIGS. 1A–1C (SEQ ID NO:1) has about 75.9% identity (using blast) in 1539 bp nucleotide residues with *Rattus norvegicus* GPR14 orphan receptor (A. Marches, et al., Genomics 29(2): 335–344, 1995). Furthermore, human GGPR14(SEQ. ID NO: 1) is 79% identical over 783 bp to *Rattus norvegicus* G-protein couple receptor SENR (M. Tal, et al., Biochem. Biophys. Res. Commun. 209(2):752–759 1995.)

One polynucleotide of the present invention encoding Human GPR14 may be obtained using standard cloning and screening, from a cDNA library derived from mRNA in cells of human placenta using the expressed sequence tag (EST) analysis (Adams, M. D., et al. *Science* (1991) 252:1651–1656; Adams, M. D. et al., *Nature,* (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

Thus, the nucleotide sequence encoding Human GPR14 polypeptides may be identical over its entire length to the coding sequence in FIGS. 1A–1C (SEQ ID NO:1), or may be a degenerate form of this nucleotide sequence encoding the polypeptide of SEQ ID NO:2, or may be highly identical to a nucleotide sequence that encodes the polypeptide of SEQ ID NO:2. Preferably, the polynucleotides of the invention contain a nucleotide sequence that is highly identical, at least 75.9% identical, with a nucleotide sequence encoding a Human GPR14 polypeptide, or at least 75.9% identical with the encoding nucleotide sequence set forth in FIGS. 1A–1C (SEQ ID NO:1), or at least 75.9% identical to a nucleotide sequence encoding the polypeptide of SEQ ID NO:2.

When the polynucleotides of the invention are used for the recombinant production of Human GPR14 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Among particularly preferred embodiments of the invention are polynucleotides encoding Human GPR14 polypeptides having the amino acid sequence of set out in FIGS. 1A–1C (SEQ ID NO:2) and variants thereof.

Further preferred embodiments are polynucleotides encoding Human GPR14 variants that have the amino acid sequence of the Human GPR14 of FIGS. 1A–1C (SEQ ID NO:2) in which several, 5–10, 1–5, 1–3, 1–2 or 1 amino acid residues are substituted, deleted or added, in any combination.

Further preferred embodiments of the invention are polynucleotides that are at least 75.9% identical over their entire length to a polynucleotide encoding the Human GPR14 polypeptide having the amino acid sequence set out in FIGS. 1A–1C (SEQ ID NO:2), and polynucleotides which are complementary to such polynucleotides. In this regard, polynucleotides at least 80% identical over their entire length to the same are particularly preferred, and those with at least 90% are especially preferred. Furthermore, those with at least 97% are highly preferred and those with at least 98–99% are most highly preferred, with at least 99% being the most preferred.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are sufficiently identical to a nucleotide sequence contained in SEQ ID NO:1, may be used as hybridization probes for cDNA and genomic DNA, to isolate full-length cDNAs and genomic clones encoding Human GPR14 and to isolate cDNA and genomic clones of other genes that have a high sequence similarity to the Human GPR14 gene. Such hybridization techniques are known to those of skill in the art. Typically these nucleotide sequences are 70% identical, preferably 80% identical, more preferably 90% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING: A LABORATORY MANUAL*, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the Human GPR14 polypeptide is to be expressed for use in screening assays, generally, it is preferred that the polypeptide be produced at the surface of the cell. In this event, the cells may be harvested prior to use in the screening assay. If Human GPR14 polypeptide is secreted into the medium, the medium can be recovered in order to recover and purify the polypeptide; if produced intracellularly, the cells must first be lysed before the polypeptide is recovered.

Human GPR14 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of Human GPR14 polynucleotides for use as diagnostic reagents. Detection of a mutated form of Human GPR14 gene associated with a dysfunction will provide a diagnostic tool that can add to or define a diagnosis of a disease or susceptibility to a disease which results from under-expression, over-expression or altered expression of Human GPR14. Individuals carrying mutations in the Human GPR14 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled Human GPR14 nucleotide sequences.

Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S I protection or the chemical cleavage method. See Cotton et al., *Proc Natl Acad Sci USA* (1985) 85: 4397–4401.

The diagnostic assays offer a process for diagnosing or determining a susceptibility to infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome through detection of mutation in the Human GPR14 gene by the methods described.

In addition, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, can be diagnosed by methods comprising determining from a sample derived from a subject an abnormally decreased or increased level of Human GPR14 polypeptide or Human GPR14 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an Human GPR14, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the Human GPR14 polypeptides. The term "immunospecific" means that the antibodies have substantiall greater affinity for the polypeptides of the invention than their affinity for other related polypeptides in the prior art.

Antibodies generated against the Human GPR14 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against Human GPR14 polypeptides may also be employed to treat infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

Vaccines

Another aspect of the invention relates to a method for inducing an immunological response in a mammal which comprises inoculating the mammal with Human GPR14 polypeptide, or a fragment thereof, adequate to produce antibody and/or T cell immune response to protect said animal from infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. Yet another aspect of the invention relates to a method of inducing immunological response in a mammal which comprises, delivering Human GPR14 gene via a vector directing expression of Human GPR14 polypeptide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a Human GPR14 polypeptide wherein the composition comprises a Human GPR14 polypeptide or Human GPR14 gene. The vaccine formulation may further comprise a suitable carrier. Since Human GPR14 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

A Human GPR14 polypeptide (receptor of the present invention) may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1(2):Chapter 5 (1991).

In general, such screening procedures involve providing appropriate cells which express a receptor polypeptide of the present invention on the surface thereof. Such cells include cells from mammals, yeast, Drosophila or *E. coli*. In particular, a polynucleotide encoding the receptor of the present invention is employed to transfect cells to thereby express a Human GPR14 polypeptide. The expressed receptor is then contacted with a test compound to observe binding, stimulation or inhibition of a functional response.

One such screening procedure involves the use of melanophores which are transfected to express a Human GPR14 polypeptide. Such a screening technique is described in PCT WO 92/01810, published Feb. 6, 1992. Such an assay may be employed to screen for a compound which inhibits activation of a receptor of the present invention by contacting the melanophore cells which encode the receptor with both a receptor ligand, such as human or fish urotensin II, and a compound to be screened. Inhibition of the signal generated by the ligand indicates that a compound is a potential antagonist for the receptor, i.e., inhibits activation of the receptor.

The technique may also be employed for screening of compounds which activate a receptor of the present invention by contacting such cells with compounds to be screened and determining whether such compound generates a signal, i.e., activates the receptor.

Other screening techniques include the use of cells which express a Human GPR14 polypeptide (for example, transfected CHO cells) in a system which measures extracellular pH changes caused by receptor activation. In this technique, compounds may be contacted with cells expressing a receptor polypeptide of the present invention. A second messenger response, e.g., signal transduction or pH changes, is then measured to determine whether the potential compound activates or inhibits the receptor.

Another screening technique involves expressing a Human GPR14 polypeptide in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists, and thus inhibit activation of a receptor polypeptide of the present invention by determining inhibition of binding of labeled ligand, such as fish or human urotensin II, to cells which have the receptor on the surface thereof, or cell membranes containing the receptor. Such a method involves transfecting a eukaryotic cell with a DNA encoding a Human GPR14 polypeptide such that the cell expresses the receptor on its surface. The cell is then contacted with a potential antagonist in the presence of a labeled form of a ligand, such as fish or human urotensin II. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called binding assay.

Another such screening procedure involves the use of mammalian cells which are transfected to express a receptor of the present invention. The cells are loaded with an indicatator dye that produces a fluorescent signal when bound to calcium, and the cells are contacted with a test substance and a receptor agonist, such as fish or human urotensin II. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist (or agonist) for the receptor.

Another such screening procedure involves use of mammalian cells which are transfected to express a receptor of the present invention, and which are also transfected with a reporter gene construct that is coupled to activation of the receptor (for example, luciferase or beta-galactosidase behind an appropriate promoter). The cells are contacted with a test substance and a receptor agonist, such as fish or human urotensin II, and the signal produced by the reporter gene is measured after a defined period of time. The signal can be measured using a luminometer, spectrophotometer, fluorimeter, or other such instrument appropriate for the specific reporter construct used. Inhibition of the signal generated by the ligand indicates that a compound is a potential antagonist for the receptor.

Another such screening technique for antagonists or agonits involves introducing RNA encoding a Human GPR14 polypeptide into Xenoputs oocytes to transiently or stably express the receptor. The receptor oocytes are then contacted with a receptor ligand, such as human or fish urotensin II, and a compound to be screened. Inhibition or activation of the receptor is then determined by detection of a signal, such as, cAMP, calcium, proton, or other ions.

Another method involves screening for a Human GPR14 polypeptide inhibitors by determining inhibition or stimulation of Human GPR14 polypeptide-mediated cAMP and/or adenylate cyclase accumulation or diminution. Such a method involves transiently or stably transfecting a eukaryotic cell with a Human GPR14 polypeptide to express the receptor on the cell surface. The cell is then exposed to potential antagonists in the presence of Human GPR14 polypeptide ligand, such as fish or human urotensin II. The amount of cAMP accumulation is then measured, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist binds the receptor, and thus inhibits Human GPR14 polypeptide binding, the levels of Human GPR14 polypeptide-mediated cAMP, or adenylate cyclase activity, will be reduced or increased.

Another screening method for agonists and antagonists relies on the endogenous pheromone response pathway in the yeast, *Saccharomyces cerevisiae*. Heterothallic strains of yeast can exist in two mitotically stable haploid mating types, MATa and MATα. Each cell type secretes a small peptide hormone that binds to a G-protein coupled receptor on opposite mating-type cells which triggers a MAP kinase cascade leading to G1 arrest as a prelude to cell fusion. Genetic alteration of certain genes in the pheromone response pathway can alter the normal response to pheromone, and heterologous expression and coupling of human G-protein coupled receptors and humanized G-protein subunits in yeast cells devoid of endogenous pheromone receptors can be linked to downstream signaling pathways and reporter genes (e.g., U.S. Pat. Nos. 5,063,154; 5,482,835; 5,691,188). Such genetic alterations include, but are not limited to, (i) deletion of the STE2 or STE3 gene encoding the endogenous G-protein coupled pheromone receptors; (ii) deletion of the FAR1 gene encoding a protein that normally associates with cyclin-dependent kinases leading to cell cycle arrest; and (iii) construction of reporter genes fused to the FUS1 gene promoter (where FUS1 encodes a membrane-anchored glycoprotein required for cell fusion). Downstream reporter genes can permit either a positive growth selection (e.g., histidine prototrophy using the FUS1-HIS3 reporter), or a colorimetric, fluorimetric or spectrophotometric readout, depending on the specific reporter construct used (e.g., β-galactosidase induction using a FUS1-LacZ reporter).

The yeast cells can be further engineered to express and secrete small peptides from random peptide libraries, some of which can permit autocrine activation of heterologously expressed human (or mammalian) G-protein coupled receptors (Broach, J. R. and Thorner, J. Nature 384: 14–16, 1996; Manfredi et al., Mol. Cell. Biol. 16: 4700–4709, 1996). This provides a rapid direct growth selection (e.g, using the FUS1-HIS3 reporter) for surrogate peptide agonists that activate characterized or orphan receptors. Alternatively, yeast cells that functionally express human (or mammalian) G-protein coupled receptors linked to a reporter gene readout (e.g., FUS1-LacZ) can be used as a platform for high-throughput screening of known ligands, fractions of biological extracts and libraries of chemical compounds for either natural or surrogate ligands. Functional agonists of sufficient potency (whether natural or surrogate) can be used as screening tools in yeast cell-based assays for identifying G-protein coupled receptor antagonists. For this purpose, the yeast system offers advantages over mammalian expression systems due to its ease of utility and null receptor background (lack of endogenous G-protein coupled receptors) which often interferes with the ability to identify agonists or antagonists.

The present invention also provides a method for determining whether a ligand not known to be capable of binding to a Human GPR14 polypeptide can bind to such receptor which comprises contacting a mammalian cell which expresses a Human GPR14 polypeptide with the ligand, such as fish or urotensin II, under conditions permitting binding of candidate ligands to a Human GPR14 polypeptide, and detecting the presence of a candidate ligand which binds to the receptor thereby determining whether the ligand binds to the Human GPR14 polypeptide. The systems hereinabove described for determining agonists and/or antagonists may also be employed for determining ligands which bind to the receptor.

Applicants further discovered that fish or human urotensin II binds equally well to rat GPR14 receptor. Thus all the above described assay techniques can be used for finding agonists and antagonists to rat GPR14 receptor by employing fish or human urotensin II as a ligand; furthermore, such identified agonists and antagonists are believed to be also agonists and antagonists to Human GPR14 polypeptides. Further aspect of present invention relates to a method of screening for agonists and antagonists of Human GPR14 polypeptides comprising screening for agonists and antagonist for rat GPR14, preferably in the presence of fish or human urotensin II.

Examples of potential Human GPR14 polypeptide antagonists include antibodies or, in some cases, oligonucleotides, which bind to the receptor but do not elicit a second messenger response such that the activity of the receptor is prevented.

Potential antagonists also include proteins which are closely related to a ligand of the Human GPR14 polypeptide, i.e. a fragment of the ligand, which have lost biological function and when binding to the Human GPR14 polypeptide, elicit no response.

Thus in another aspect, the present invention relates to a screening kit for identifying agonists, antagonists, and ligands for Human GPR14 polypeptides, which comprises:
(a) rat GPR14 or a Human GPR14 polypeptide, preferably that of SEQ ID NO:2, and preferably further comprises labeled or unlabeled fish or human urotensin II;
(b) a recombinant cell expressing rat GPR14 or a Human GPR14 polypeptide, preferably that of SEQ ID NO:2, and preferably further comprises labeled or unlabeled fish or human urotensin II; or
(c) a cell membrane expressing rat GPR14 or a Human GPR14 polypeptide; preferably that of SEQ ID NO: 2, and preferably further comprises labeled or unlabled fish or human urotensin II.

It will be appreciated that in any such kit, (a), (b), or (c) may comprise a substantial component.

A potential antagonist also includes an antisense construct prepared through the use of antisense technology. Antisense technology can be used to control gene expression through triple-helix formation or antisense DNA or RNA, both methods of which are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee, et al. *Nucl. Acids Res.*, 6:

3073 (1979); Cooney, et al, *Science,* 241: 456 (1988); and Dervan, et al., *Science,* 251: 1360 (1991)), thereby preventing transcription and production of a Human GPR14 polypeptide. The antisense RNA oligonucleotide hybridizes to the mRNA in vivo and blocks translation of the mRNA molecule to a Human GPR14 polypeptide (antisense—Okano, J., *Neurochem.,* 56: 560 (1991); OLIGODEOXYNUCLEOTIDES AS ANTISENSE INHIBITORS OF GENE EXPRESSION, CRC Press, Boca Raton, Fla. (1988)). The oligonucleotides described above can also be delivered to cells such that the antisense RNA or DNA may be expressed in vivo to inhibit production of a Human GPR14 polypeptide.

Another potential antagonist is a small molecule which binds to a Human GPR14 polypeptide, making it inaccessible to ligands such that normal biological activity is prevented. Examples of small molecules include, but are not limited to, small peptides or peptide-like molecules.

Potential antagonists also include soluble forms of a Human GPR14 polypeptide, e.g., fragments of the polypeptide, which bind to the ligand and prevent the ligand from interacting with membrane bound Human GPR14 polypeptides.

Human GPR14 proteins are ubiquitous in the mammalian host and are responsible for many biological functions, including many pathologies. Accordingly, it is desirous to find compounds and drugs which stimulate Human GPR14 on the one hand and which can inhibit the function of Human GPR14 on the other hand. In general, agonists are employed for therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome. Antagonists may be employed for a variety of therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

Prophylactic and Therapeutic Methods

This invention provides methods of treating an abnormal conditions related to both an excess of and insufficient amounts of Human GPR14 activity.

If the activity of Human GPR14 is in excess, several approaches are available. One approach comprises administering to a subject an inhibitor compound (antagonist) as hereinabove described along with a pharmaceutically acceptable carrier in an amount effective to inhibit activation by blocking binding of ligands to the Human GPR14, or by inhibiting a second signal, and thereby alleviating the abnormal condition.

In another approach, soluble forms of Human GPR14 polypeptides still capable of binding the ligand in competition with endogenous Human GPR14 may be administered. Typical embodiments of such competitors comprise fragments of the Human GPR14 polypeptide.

In still another approach, expression of the gene encoding endogenous Human GPR14 can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression,* CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of Human GPR14 and its activity, several approaches are also available. One approach comprises administering to a subject a therapeutically effective amount of a compound which activates Human GPR14, i.e., an agonist as described above, in combination with a pharmaceutically acceptable carrier, to thereby alleviate the abnormal condition. Alternatively, gene therapy may be employed to effect the endogenous production of Human GPR14 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches,* (and references cited therein) in Human Molecular Genetics, T Strachan and A P Read, BIOS Scientific Publishers Ltd (1996).

Formulation and Administration

Peptides, such as the soluble form of Human GPR14 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

A 1.2 kb PCR fragment corresponding to the entire coding region of the *Rattus norvegicus* orphan receptor (GPR14, A. Marchese et al. Genomics, 29(2): 335–44, 1995) was used as a probe to screen a total of 0.75M plaques from a Human Genomic Placenta library (Stratagene, Latolla Calif., Cat. # 946206). The genomic library screening procedure is described by (Elgin, et al. Stratagies 4: 8–9, 1991). The probes were α-32P labeled, using Random Primed Labeling Kit (Boheringer Manheim, Germany, Cat. # 1585584) and purified by running over Sephadex G-50 columns (Pharmacia Biotech. Cat. # 17-0855-02) The hybirdization and washing conditions were according to (J. Sambrook, E. F. Fritch and T. Maniatis (1989) A Laboratory Manaul Second. Ed. Vol. 1 pp. 2.69–2.81 Cold Spring Harbor Laboratory Press, Cold Spring Harbor, N.Y.). One Positive phage clone obtained form above screen was further purified. Southern analysis were carried out on digested phage DNA and a 9 kb Sac I fragment hybirdized for this clone. This fragment was subcloned into pBlueScript KS vector, and further digested with EcoRI and southern analyzed. A smaller 5 kb fragment hybirdized to the rat GPR14 probe mentioned above was subcloned into pBlueScript for sequence analysis, the sequence was determined by automated sequencer. A total of 2126 bp were sequenced, this includes an open reading frame enconding a peptide of 390 residues. This sequence is highly homologus to Rat GPR14, as shown by sequence comparisons and also by fasta analysis against the Genbank nucleotid data base.

Example 2
Mammalian Cell Expression

The receptors of the present invention are expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN or pCDNA3 vector. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectably in about 50% of the G418-resistant clones analyzed.

Example 3
Ligand bank for binding and functional assays.

A bank of over 200 putative receptor ligands has been assembled for screening. The bank comprises: transmitters, hormones and chemokines known to act via a human seven transmembrane (7TM) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e. calcium, cAMP, microphysiometer, oocyte electrophysiology, etc, see below) as well as binding assays.

Example 4
Ligand Binding Assays

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

Example 5
Functional Assay in Xenopus Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/ml. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure. Recordings are made in Ca2+ free Barth's medium at room temperature. The Xenopus system can be used to screen known ligands and tissue/cell extracts for activating ligands.

Example 6
Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

Example 7
Extract/Cell Supernatant Screening

A large number of mammalian receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequencially subfractionated until an activating ligand is isolated identified.

Example 8
Calcium and cAMP Functional Assays

7TM receptors which are expressed in HEK 293 cells have been shown to be coupled functionally to activation of PLC and calcium mobilization and/or cAMP stimuation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day>150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP flucuation are tested in vector control cells to determine if the response is unique to the transfected cells expressing receptor.

Example 9
Urotensin II-induced Ca2+ mobilization in transient HEK 293 GPR14 and stable HEK 293 Gα16 GPR14 cells.

Figure 4:
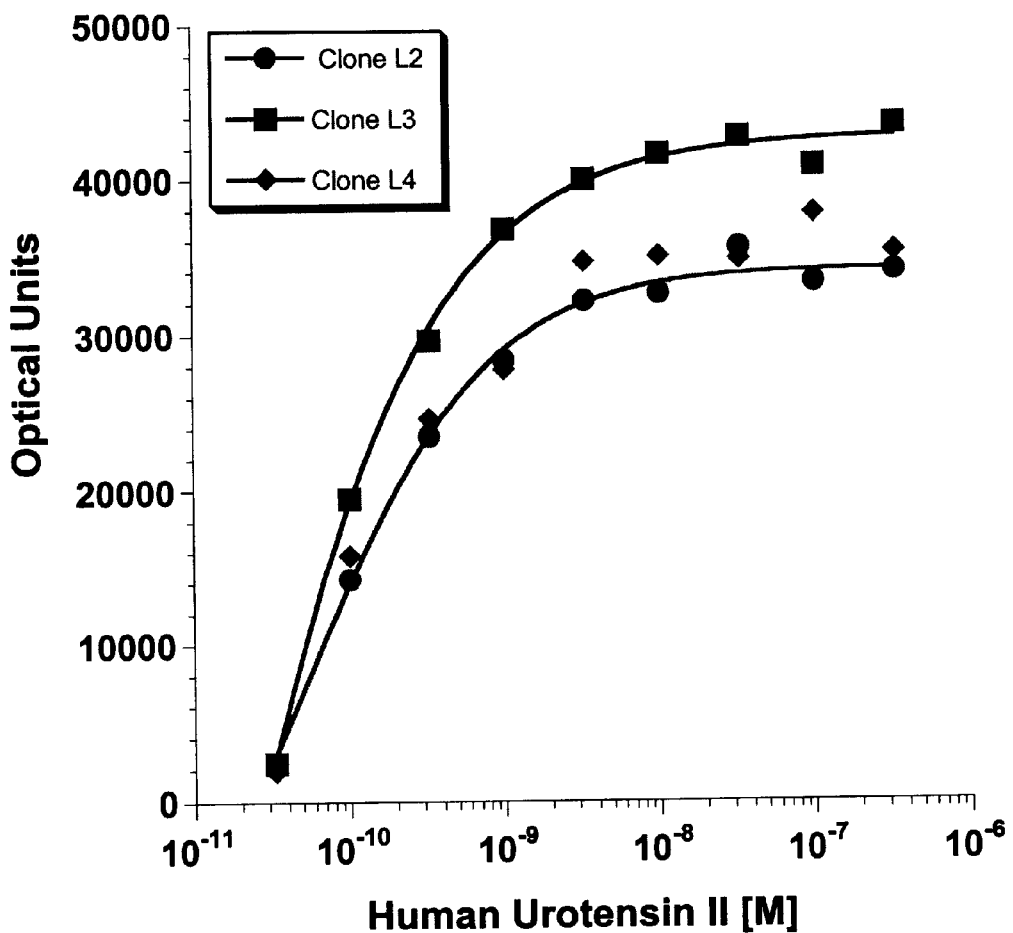
FIG. 4 is the concentration-response-curves for human urotensin II for 3 clones of the Human GPR 14 stably transfected cells.

The GPR14 receptor when transiently transfected into HEK 293 cells responds to urotensin II in a concentration-dependent manner with a robust calcium response. Both the transiently transfected rat and human receptors respond to fish urotensin II with similar affinities. FIG. 3 shows the concentration response curves for fish urotensin II against both the rat and human receptors. The data was generated with the 96 well FLuorescent Imaging Plate Reader (FLIPR). Each point is the mean of 6–8 individual wells in 3–4 separate 96 well plates read on FLIPR. The EC50 for fish urotensin II was 0.5 nM for the human receptor and 0.8 nM for the rat receptor. Additionally the human receptor was stably transfected into HEK 293 Gα16 cells and human urotensin II produced concentration dependent calcium mobilization responses. FIG. 4 is the concentration-response-curves for human urotensin II for 3 clones (designated L2, L3 and L4) of the stably transfected cells. The EC50s of human urotensin II for the 3 clones were 0.1–0.2 nM.

What is claimed is:

1. An isolated polypeptide comprising at least one sequence fragment selected from the group consisting of amino acids 1–20, 21–40, 41–60, 61–80, 81–100, and 101–389 of the amino acid sequence set forth in SEQ ID NO:2.

2. The isolated polypeptide of claim 1 comprising amino acids 1–20 of the amino acid sequence set forth in SEQ ID NO:2.

3. The isolated polypeptide of claim 1 comprising amino acids 21–40 of tie amino acid sequence set forth in SEQ ID NO:2.

4. The isolated polypeptide of claim 1 comprising amino acids 41–60 of the amino acid sequence set forth in SEQ ID NO:2.

5. The isolated polypeptide of claim 1 comprising amino acids 61–80 of the amino acid sequence set forth in SEQ ID NO:2.

6. The isolated polypeptide of claim 1 comprising amino acids 81–100 of the amino acid sequence set forth in SEQ ID NO:2.

7. The isolated polypeptide of claim 1 comprising amino acids 101–389 of the amino acid sequence set forth in SEQ ID NO:2.

* * * * *